(12) United States Patent
Allmon

(10) Patent No.: US 6,210,373 B1
(45) Date of Patent: Apr. 3, 2001

(54) NEEDLE SAFETY COVER

(75) Inventor: Butch Allmon, Paradise, TX (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/476,424

(22) Filed: Dec. 30, 1999

(51) Int. Cl.$^7$ ............................................. A61M 5/00
(52) U.S. Cl. ................................... 604/192; 604/110
(58) Field of Search ............................. 604/263, 110, 604/198, 192

(56) References Cited

U.S. PATENT DOCUMENTS

| 4,929,241 | 5/1990 | Kulli . |
| 4,952,207 | 8/1990 | Lemieux . |
| 4,964,854 | 10/1990 | Luther . |
| 4,978,344 | 12/1990 | Dombrowski et al. . |
| 5,049,136 | 9/1991 | Johnson . |
| 5,085,648 | 2/1992 | Purdy et al. . |
| 5,092,845 | 3/1992 | Chang . |
| 5,135,504 | 8/1992 | McLees . |
| 5,147,327 | 9/1992 | Johnson . |
| 5,215,528 | 6/1993 | Purdy et al. . |
| 5,344,408 * | 9/1994 | Partika .................. 604/192 |
| 5,419,766 | 5/1995 | Chang et al. . |
| 5,601,536 | 2/1997 | Crawford et al. . |
| 5,662,610 * | 9/1997 | Sircom ................... 604/110 |
| 5,697,907 * | 12/1997 | Gaba ................... 604/198 X |

* cited by examiner

Primary Examiner—John D. Yasko
(74) Attorney, Agent, or Firm—Blakely, Sokoloff, Taylor & Zafman

(57) ABSTRACT

An apparatus was disclosed comprising a housing having a proximal end and a distal end, the housing slidably mounted on a needle shaft below a needle distal tip, the clip having a bridge, a proximal end coupled to the bridge and a distal end coupled to the bridge. The clip is disposed within the housing such that it retains a resilience imparting a biasing force to the clip ends such that the ends grip the needle shaft. When the housing is advanced beyond the needle distal tip, the clip distal end releases to contain the needle distal tip within the housing.

10 Claims, 3 Drawing Sheets

NEEDLE SAFETY COVER

FIELD OF THE INVENTION

This invention relates to the field of medical devices and in particular to a needle safety cover.

BACKGROUND

Blood borne diseases such as AIDS and Hepatitis present significant risks to medical personnel administering vascular injections. The means by which a patient's vessel and skin are pierced to either draw or introduce fluids can just as effectively pierce the hands and arms of attending medical personnel. Gloves or similar protective garb may provide some protection, but making such items entirely resistant to needle penetration oftentimes sacrifices the wearer's mobility and dexterity proportionate to the degree of protection. Therefore, protective wear is not a total answer to the problem.

In order to adequately protect medical personnel from inadvertent puncture and wounding, catheter systems have been developed to cover and shield the distal needle point after its withdrawal from the patient. These systems have taken a number of embodiments and have various degrees of elaboration. One such mechanism includes a cylindrical sheath of plastic which telescopes out from the flash chamber to surround the needle shaft, including the distal tip. Such mechanism increases costs of manufacture substantially and may malfunction, especially in a fluid filled environment where it may stick or slip. The need for locking parts under these circumstances also increases risk of failure. Other types of needle caps require moving parts, such as a spring activation, to close off the needle in the cap after its withdrawal. These sometimes combine moving parts with specially tooled needles having two or more separate widths so that the larger circumference and diameter either trips the spring and/or blocks the needle's removal from the cap.

Given that the needle protector, however configured, will be contaminated upon each use, cost-benefit requirements dictate that a desirable shielding system be disposable along with the needle. Furthermore, the system must be quick and easy to use as to present as little imposition as possible to the administration and function of the catheter. Moving parts which may malfunction or stick such as springs and similar biasing mechanisms, as well as telescoping sheaths requiring deployment from the flash chamber, are less desirable in this regard and can drive up the manufacturing cost for a disposable unit. Lathing the needle circumference to alter the circumference over particular segments requires precise tooling and hence substantially added cost. What is desirable is a low cost, easily manufactured needle cover.

SUMMARY

An apparatus is disclosed comprising a housing having a proximal end and a distal end, the housing slidably mounted on a needle shaft below a needle distal tip, the clip having a bridge, a proximal end coupled to the bridge and a distal end coupled to the bridge. The clip is disposed within the housing such that it retains a resilience imparting a biasing force to the clip ends such that the ends grip the needle shaft. When the housing is advanced beyond the needle distal tip, the clip distal end releases to contain the needle distal tip within the housing.

Other features and advantages of the invention will be apparent from the accompanying drawings and from the detailed description that follows below.

BRIEF DESCRIPTION OF THE DRAWINGS

The invention is illustrated by way of example and not by way of limitation in the figures of the accompanying drawings in which like references indicate similar elements and in which.

DETAILED DESCRIPTION

Figure 1:
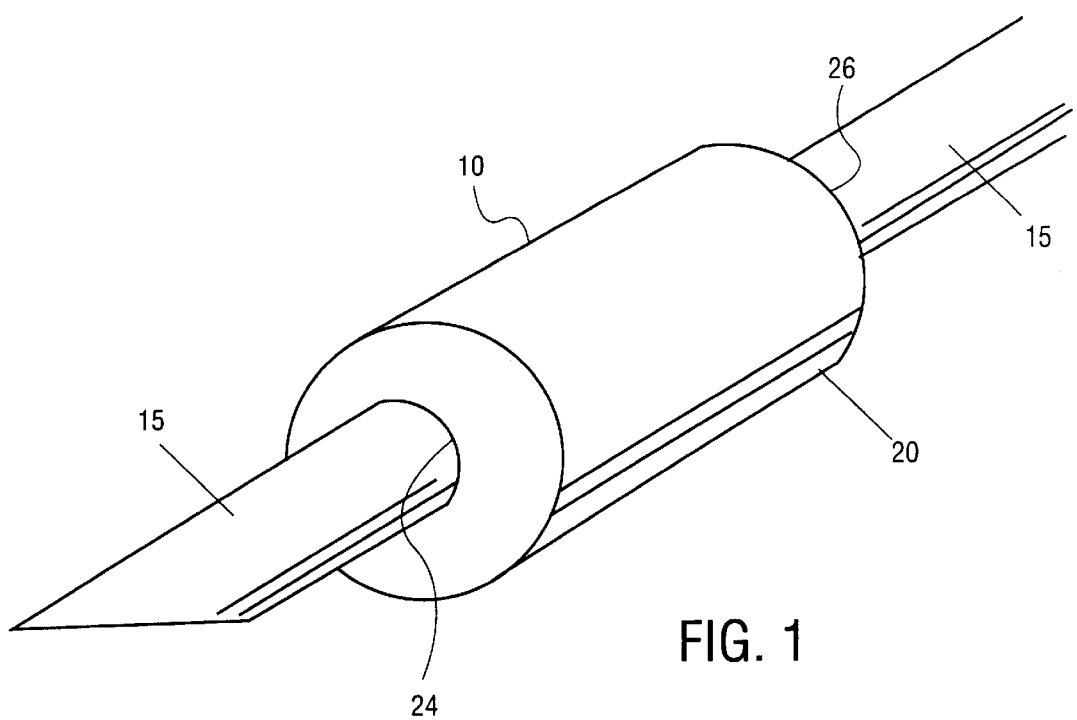
FIG. 1 shows a perspective view of an embodiment of the invention as fit over a needle shaft.

FIG. 1 shows one embodiment of the invention where needle cover 10 is mounted upon a needle shaft 15. In this embodiment, housing 20 for needle cover 10 is barrel shaped. Needle cover 10 is slidably mounted on needle shaft 15 and prior to its deployment, is located back from the needle distal tip (not pictured) such that the shaft extends through housing 20 of the needle cover 10. For ease of sliding, needle shaft 15 may be lubricated or coated.

Figure 2:
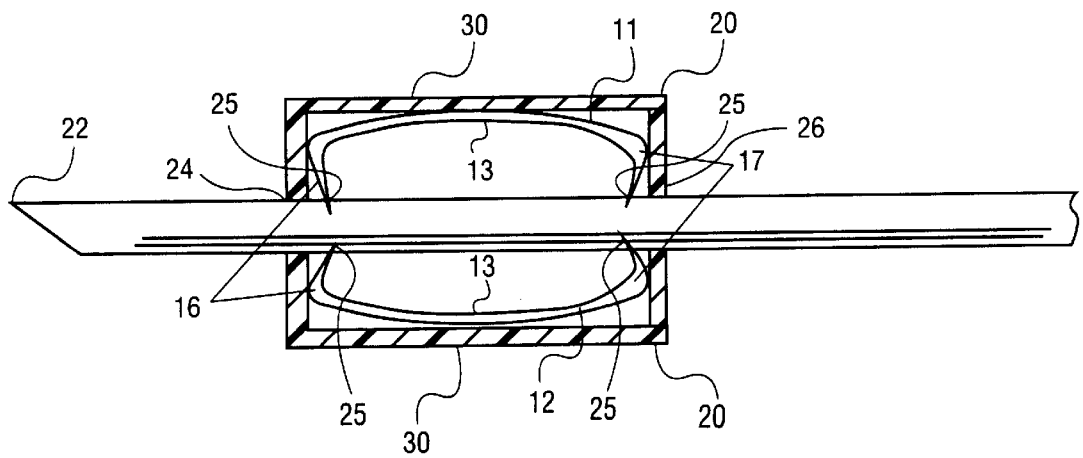
FIG. 2 shows a cutaway side view of one embodiment of the invention as fit over a needle shaft.

With reference to FIG. 2, needle shaft 15 and distal tip 22 are illustrated with one embodiment of the invention mounted thereon. In this embodiment, the invention includes housing 20 defining openings 24, 26 at the proximal and distal ends, respectively, to accommodate needle shaft 15 extending therethrough. The openings have diameters slightly larger than needle shaft 15 outer diameter so that the housing 20 slides along needle shaft 15 and contacts substantially the entire needle shaft 15 outer circumference. Inside housing 20 are clips 11, 12. In one embodiment, clips 11, 12 each having bridge 13 and two legs 16, 17 coupled to bridge 13 at opposite ends. In one embodiment, bridge 13 may be arched with the apex of the arch approaching or engaging horizontal walls 30 of housing 20. Clips 11, 12 are loaded into housing 20 under a compressive force which biases legs 16, 17 toward needle shaft 15. In one embodiment, housing 20 is made of a polymer and clips 11 and 12 are loaded as housing 20 is injection molded. Clips 11, 12 may be made of resilient material so as to impart a memory upon bending or contorting clips 11, 12 into housing 15 when loaded. As such, housing 15 and clips 11, 12 can be of a complementary size to accommodate biased clips 11, 12 and fit them within the housing.

Clip legs 16, 17 terminate in tabs 25 which define a semicircular circumference to fit around needle shaft 15. This allows for a more close fit of tabs 25 to the needle shaft 15 increasing their grip thereon. In one embodiment, tab ends (not pictured) are not equivalent lengths, rather one is shorter than the other. The resulting arc, of the defined circumference therefore is eccentric. Such configuration allows for a greater ability to grip needle shaft 15 when legs 16, 17 are contorted to engage needle shaft 15 at an angle to bridge 13 less then 90 degrees, providing for greater constrictive force, imparting greater potential energy to the bias resilience than engaging needle shaft 15 at a 90 degree angle where legs 16, 17 are directed toward needle shaft 15. The angular engagement of legs 16, 17 of the opposing tabs at the proximal end of housing 20 also provide greater restrictive force opposing advancement of housing 20 toward distal end 22 of needle shaft 15, thus obstructing removal of housing 20 over distal tip 22 when legs 16 have deployed over distal tip 22.

Figure 3:
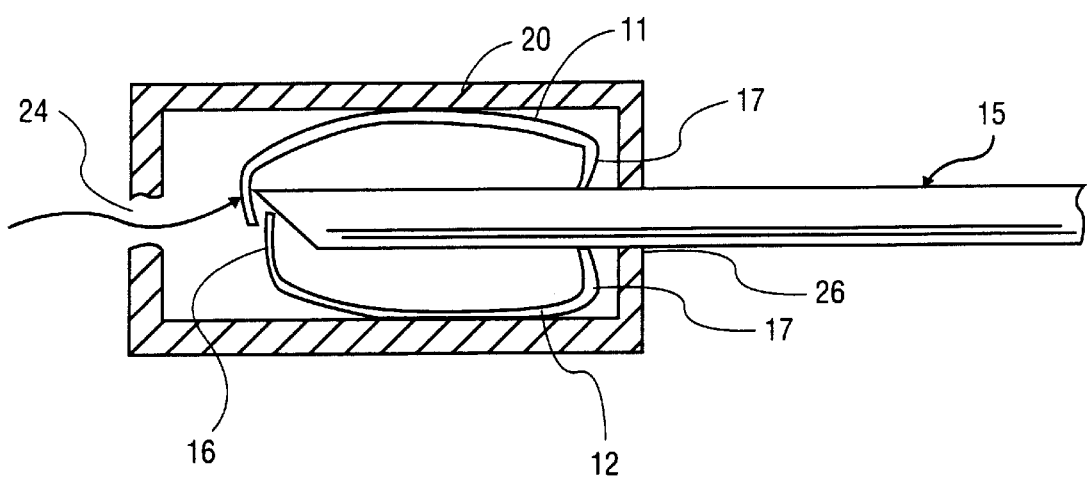
FIG. 3 shows a cutaway side view of one embodiment of the invention as deployed over the distal tip of the needle.

FIG. 3 shows the result of sliding housing 20 over distal tip 22 of the needle shaft 15. As tabs 25 of front legs 16 of clips 13 are biased against the needle shaft, advancing the cover 10 over distal tip 22 and past the point of contact with tabs 25 of front legs 16, causes legs 16 to release with resilient force to fit over distal tip 22. In another embodiment, the two opposing legs 16 and tab ends 25 may meet and rest on each other—either eliminating or so constricting the area between tabs 25 to a size smaller than the needle outer diameter, including the outer diameter at the distal tip 22, so that reinsertion through front opening 24 is blocked.

As the front legs 16 deploy, by resilient force, over distal tip 15 to block its reinsertion through opening 24, rear legs 17, given their obtuse angles to needle shaft 15, inhibit further frontal movement of housing 20 toward distal tip 22 thus preventing removal of the housing 20 over distal tip 22 and obstructing sliding housing 20 too far forward on needle shaft 15, thus falling off distal tip 22.

Figure 4:
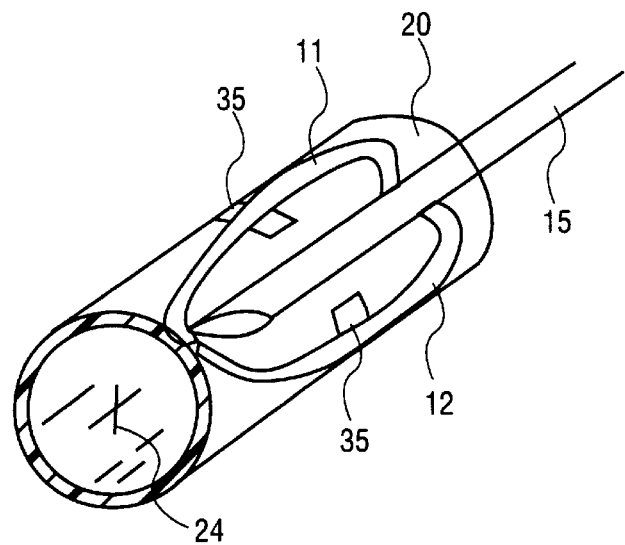
FIG. 4 shows a perspective cutaway view of one embodiment of the invention deployed over the distal tip.

FIG. 4 shows an embodiment of the invention, where housing 20 is barrel shaped having a cylindrical configuration. Transparent windows 35 on opposing sides of the housing allow the user to view inside to determine if distal point 22 is contained therein, and thus blocked from reinsertion through opening 24. In one embodiment, windows 35 are located at a point equivalent to the distance distal point 22 would occupy upon deployment of clip legs 16. Inability to view distal tip 22 could then indicate clip legs 16 had not deployed and distal tip 22 could still re-emerge from distal opening 24 of the housing.

The housing is made from materials and in manners known in the art for catheter accessories such as polyurethane and other polymer materials. It may be injection molded in accordance with the practice of the art. Metal reinforcing may be used to provide further support and strength within the polymer mix or the injection molding process.

Figure 5:
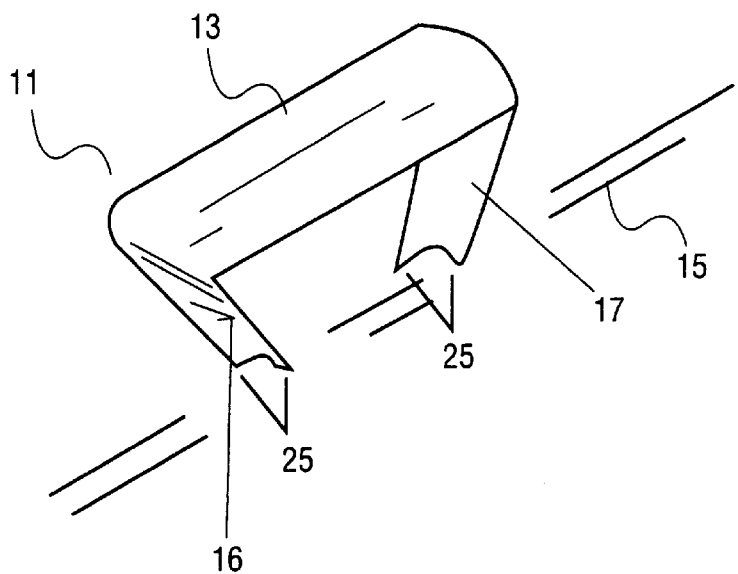
FIG. 5 shows a perspective view of a clip of one embodiment of the invention.

FIG. 5 shows a metal clip 11. Clip 11 is bent at two ends to form legs 16 and 17, according to methods known in the art. In one embodiment bridge 13 is arched to provide greater biasing force to legs 16 and 17. Another embodiment allows the bridge 13 to remain substantially horizontal in relation to shaft 15 while legs 16, 17 are bent to form an angle to bridge 13 of less than 90 degrees and the biasing force imparted is analogous to a hinging force at the point of connection between bridge 13 and legs 16, 17 which impels legs 16, 17 to return to a straight or substantially perpendicular orientation with respect to bridge 13. Heat treatment of legs 16,17 may be used to provide the biasing memory and hinge resilience. Clip legs 16, 17 culminate in tabs 25 which define a semicircular circumferential surface for gripping needle shaft 15. In one embodiment, tabs 25 on each clip 11,12 define a semicircular circumference with sides not equivalent in length, and thus define an eccentric semicircle. Where clips 11, 12 engage needle shaft 15 using hinged legs 16, 17, thus meeting needle shaft 15 to create a hinge angle less than 90 degrees, the irregular tab lengths serve to keep the surface area gripping needle shaft 15 relatively constant and ensure a complete fit, with the longer tab side length directing the tabs along the circumference of the needle shaft 15 to the center of the tabs at the semicircle apex thus providing sufficient support to avoid slippage.

Figure 6:
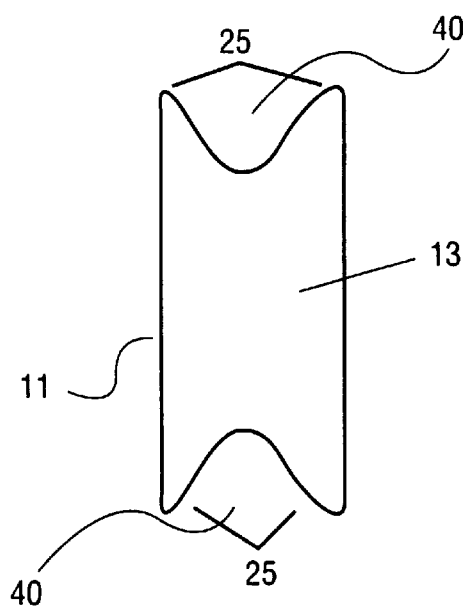
FIG. 6 shows a top view of a flat metal piece prior to its bending to form a clip of one embodiment of the invention.

FIG. 6 illustrates clip 11 in a flat view before bending, illustrating tabs 25 and the semicircular space 40 they define to receive the needle shaft. Bending of legs 16, 17 where tabs 25 are located may be done by heat treatment to impart biasing memory and, in one embodiment, to arch bridge 13. In one embodiment, the bending can also be accomplished by a foreslide machine. Clips may be pressed or stamped from sheets. The clips may be made of any suitable metal alloy known in the art. In one embodiment, these are stainless steel.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus comprising:
    a housing having a proximal end and a distal end, the housing slidably mounted on a needle shaft below a needle distal tip;
    a first clip having a bridge, a proximal end coupled to the bridge and a distal end coupled to the bridge, the first clip disposed within the housing such that it retains a resilience imparting a biasing force to the first clip ends such that the ends grip the needle shaft and when the housing is advanced beyond the needle distal tip, the first clip distal end releases to contain the needle distal tip within the housing; and
    a second clip having a bridge, a proximal end coupled to the bridge and a distal end coupled to the bridge, the second clip disposed within the housing such that it retains a resilience imparting a biasing force to the second clip ends such that the ends grip the needle shaft and when the housing distal end is advanced beyond the needle distal tip, the second clip distal end releases to contain the needle distal tip within the housing.

2. The apparatus of claim 1, wherein the distal end of the first clip and the distal end of the second clip engage each other upon their release to contain the needle distal tip within the housing.

3. The apparatus of claim 1, wherein the first and second clip ends terminate in tabs which define a semicircular circumference configured to receive the needle shaft.

4. The apparatus of claim 1, wherein the first clip and the second clip each further comprise an arched bridge coupled to the distal end and the proximal end.

5. The apparatus of claim 1, wherein the first clip and second clip proximal ends and distal ends are hinged to the bridge such that the angle formed by the hinges is less than ninety degrees when the clip proximal end and distal end engage the needle shaft.

6. The apparatus of claim 5, wherein the proximal ends of the first clip and second clip engage the needle shaft so as to obstruct advancement of the housing toward the needle distal tip when the distal ends of the first clip and second clip release.

7. The apparatus of claim 2, wherein the first and second clips are fashioned from stainless steel.

8. The apparatus of claim 1 wherein the housing further defines a window for viewing the needle distal tip when contained within the housing.

9. The apparatus of claim 1, wherein the housing is barrel shaped.

10. The apparatus of claim 3, wherein the tabs define an eccentric semicircular circumference having sides of substantially inequivalent lengths.

* * * * *